(12) United States Patent
Lu et al.

(10) Patent No.: US 11,366,946 B2
(45) Date of Patent: Jun. 21, 2022

(54) METHOD AND APPARATUS FOR OBTAINING SURFACE POTENTIAL

(71) Applicant: THE INSTITUTE OF MICROELECTRONICS OF CHINESE ACADEMY OF SCIENCES, Beijing (CN)

(72) Inventors: Nianduan Lu, Beijing (CN); Ling Li, Beijing (CN); Ming Liu, Beijing (CN)

(73) Assignee: THE INSTITUTE OF MICROELECTRONICS OF CHINESE ACADEMY OF SCIENCES, Beijing (CN)

( * ) Notice: Subject to any disclaimer, the term of this patent is extended or adjusted under 35 U.S.C. 154(b) by 308 days.

(21) Appl. No.: 16/646,573

(22) PCT Filed: Aug. 9, 2018

(86) PCT No.: PCT/CN2018/099637
§ 371 (c)(1),
(2) Date: Mar. 12, 2020

(87) PCT Pub. No.: WO2019/232921
PCT Pub. Date: Dec. 12, 2019

(65) Prior Publication Data
US 2020/0265176 A1      Aug. 20, 2020

(30) Foreign Application Priority Data
Jun. 7, 2018   (CN) .......................... 201810577635.6

(51) Int. Cl.
*G06F 30/27*   (2020.01)
*G06F 16/23*   (2019.01)
(Continued)

(52) U.S. Cl.
CPC .......... *G06F 30/27* (2020.01); *G06F 16/2379* (2019.01); *G06N 3/08* (2013.01); *G06F 2111/10* (2020.01)

(58) Field of Classification Search
None
See application file for complete search history.

(56) References Cited

U.S. PATENT DOCUMENTS

2015/0242546 A1* 8/2015  Jeon ................... G06F 30/20
                                                               703/2
2019/0102908 A1* 4/2019  Yang ................... G06V 10/25
2020/0310366 A1* 10/2020 Tsumura ............... B33Y 50/00

FOREIGN PATENT DOCUMENTS

CN    102508942 A    6/2012
CN    103186691 A    7/2013
CN    105468828 A    4/2016

OTHER PUBLICATIONS

International search report of PCT/CN2018/099637.

* cited by examiner

*Primary Examiner* — Craig C Dorais

(57) ABSTRACT

The present disclosure provides a method and an apparatus for obtaining surface potential. The method comprises: obtaining parameter information of multiple target devices, wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined, and the conventional materials include bulk materials and the first new materials include thin film materials; extracting surface potentials based on the size, the device structure, the material parameter and the mobility of each of the target (Continued)

devices under corresponding operating conditions; establishing a surface potential database based on the surface potentials and the parameter information; constructing a surface potential analytical model according to neural network based on the surface potential database; and determining the surface potential of a device fabricated by using a second new material by using the surface potential analytical model.

10 Claims, 2 Drawing Sheets

(51) Int. Cl.
*G06N 3/08* (2006.01)
*G06F 111/10* (2020.01)

```
┌─────────────────────────────────────────────────────────────┐
│ obtaining parameter information of multiple target devices, │  ┌─ S110
│ wherein the parameter information includes: size, device    │──┘
│ structure, material parameter, and carrier mobility of each │
│ of the target devices at different temperatures             │
└─────────────────────────────────────────────────────────────┘
                              │
                              ▼
┌─────────────────────────────────────────────────────────────┐
│ extracting surface potentials based on the size, the device │  ┌─ S111
│ structure, the material parameter and the mobility of each  │──┘
│ of the target devices under corresponding operating         │
│ conditions                                                  │
└─────────────────────────────────────────────────────────────┘
                              │
                              ▼
┌─────────────────────────────────────────────────────────────┐
│ establishing a surface potential database based on the      │  ┌─ S112
│ surface potentials and the parameter information            │──┘
└─────────────────────────────────────────────────────────────┘
                              │
                              ▼
┌─────────────────────────────────────────────────────────────┐
│ constructing a surface potential analytical model according │  ┌─ S113
│ to neural network based on the surface potential database   │──┘
└─────────────────────────────────────────────────────────────┘
                              │
                              ▼
┌─────────────────────────────────────────────────────────────┐
│ determining the surface potential of a device made of a     │  ┌─ S114
│ second new material by using the surface potential          │──┘
│ analytical model                                            │
└─────────────────────────────────────────────────────────────┘
```

FIG. 1

METHOD AND APPARATUS FOR OBTAINING SURFACE POTENTIAL

TECHNICAL FIELD

The disclosure relates to the technical field of semiconductor devices, and particularly relates to a method and an apparatus for obtaining surface potential.

BACKGROUND OF THE INVENTION

Semiconductor device models are indispensable part of the semiconductor industry as a bridge between semiconductor manufacturers and circuit designers.

With the development of semiconductor devices, many new materials have appeared. In order to improve the simulation accuracy of devices, researchers generally use surface potentials to study devices of new materials, and need to obtain corresponding surface potentials to study physical characteristics of devices fabricated by using new materials. However, the methods for obtaining surface potentials of devices fabricated by using new materials in the prior art is relatively complicated, and the efficiency of obtaining the surface potentials is not high, resulting in low efficiency in research process.

SUMMARY OF THE INVENTION

To address the problems existing in the prior art, the embodiments of the present disclosure provide a method and an apparatus for obtaining surface potential, solving the problems in the prior art that the existing methods of obtaining surface potential of a new material surface potential device are complicated, the efficiency thereof is low, and the process for studying the characteristics of a new material surface potential device using surface potential is progressed slowly.

Embodiments of the disclosure provide a method for obtaining surface potential, and the method may comprise:

obtaining parameter information of multiple target devices, wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined, and the conventional materials include bulk materials, and the first new materials include thin film materials;

extracting surface potentials based on the size, the device structure, the material parameter and the mobility of each of the target devices under corresponding operating conditions;

establishing a surface potential database based on the surface potentials and the parameter information;

constructing a surface potential analytical model according to neural network based on the surface potential database; and determining the surface potential of a device fabricated by using a second new material by using the surface potential analytical model.

In some embodiments, obtaining carrier mobility of each of the target devices at different temperatures may include:

obtaining the carrier mobility $\mu(T)$ according to a formula $$\mu(T) = \frac{qa}{k_B T} v_0 \exp\left(-\frac{E_a}{k_B T}\right),$$

where q represents elementary charge, a represents atomic separation, $k_B$ represents Boltzmann constant, T represents temperature, $v_0$ represents reciprocal of length of localized state, and $E_a$ represents activation energy of carrier transition.

In some embodiments, the establishing a surface potential database based on the surface potentials and the parameter information may include:

establishing mapping tables between the surface potentials and the parameter information; and respectively storing the mapping tables in corresponding data blocks in a preset database to form the surface potential database.

In some embodiments, constructing the surface potential analytical model according to neural network based on the surface potential database may include:

determining a surface potential training sample set based on the surface potential database; and performing data fitting on the surface potential training sample set by using a hypothesis model provided by the neural network so as to obtain a physical equation, and the physical equation is the surface potential analytical model.

In some embodiments, after constructing the surface potential analytical model according to neural network based on the surface potential database, the method may further comprise:

establishing a Schrödinger-Poisson equation based on the surface potential database;

obtaining a first solution of the Schrödinger-Poisson equation by using a self-consistent solution;

obtaining a second solution of the surface potential analytical model;

obtaining a difference between the second solution and the first solution; and verifying the surface potential analytical model by using the difference The present disclosure also provides an apparatus for obtaining surface potential, and the apparatus may comprise:

an obtaining unit, configured for obtaining parameter information of multiple target devices, wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined, and the conventional materials include bulk materials, and the first new materials include thin film materials;

an extracting unit, configured for extracting surface potentials based on the size, the device structure, the material parameter, and the mobility of each of the target devices under corresponding operating conditions;

an establishing unit, configured for establishing a surface potential database based on the surface potentials and the parameter information;

a constructing unit, configured for constructing a surface potential analytical model according to neural network based on the surface potential database; and a determining unit, configured for determining the surface potential of a device fabricated by using a second new material by using the surface potential analytical model.

In some embodiments, the second obtaining unit may be specifically configured for:

obtaining the carrier mobility µ(T) according to a formula $$\mu(T) = \frac{qa}{k_B T} v_O \exp\left(-\frac{E_a}{k_B T}\right),$$

where q represents elementary charge, a represents atomic separation, $k_B$ represents Boltzmann constant, T represents temperature, $v_O$ represents reciprocal of length of localized state, and $E_a$ represents activation energy of carrier transition.

In some embodiments, the establishing unit may be specifically configured for:

establishing mapping tables between the surface potentials and the parameter information; and respectively storing the mapping tables in corresponding data blocks in a preset database to form the surface potential database.

In some embodiments, the constructing unit may be specifically configured for:

determining a surface potential training sample set based on the surface potential database; and performing data fitting on the surface potential training sample set by using a hypothesis model provided by the neural network so as to obtain a physical equation, and the physical equation is the surface potential analytical model.

In some embodiments, the apparatus may further comprise a verifying unit configured for:

establishing a Schrödinger-Poisson equation based on the surface potential database;

obtaining a first solution of the Schrödinger-Poisson equation by using a self-consistent solution;

obtaining a second solution of the surface potential analytical model;

obtaining a difference between the second solution and the first solution; and verifying the surface potential analytical model by using the difference.

The disclosure provides a method and an apparatus for obtaining surface potential. The method may comprise: obtaining parameter information of multiple target devices, and wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined; extracting the surface potentials based on the size, the device structure, the material parameter, and the mobility of each of the target devices under corresponding operating conditions; establishing a surface potential database based on the surface potentials and the parameter information; constructing a surface potential analytical model according to neural network based on the surface potential database; and determining the surface potential of a device fabricated by using a new material by using the surface potential analytical model. Therefore, multiple target devices of different structures and different materials are used to obtain multiple surface potentials under different operating conditions; then a surface potential database is established based on these surface potentials, and a surface potential analytical model is constructed by using neural network, and a surface potential of a device fabricated by using a new material is determined by using the surface potential analytical model. Because the surface potential analytical model constructed is equivalent to an intelligent analytical model obtained by normalizing devices under various structures, various parameters, and various conditions, when a surface potential of a device fabricated by using a new material is determined by using the surface potential analytical model, a corresponding surface potential can be quickly determined according to some parameters of the device fabricated by using the new material, so that the surface potential can be obtained without complicated testing, improving the efficiency of obtaining surface potential, and also improving the efficiency of the overall research process when studying some characteristics of surface potential devices fabricated by using new materials with the surface potentials.

BRIEF DESCRIPTION OF THE DRAWINGS

Various other advantages and benefits will become apparent to those of ordinary skill in the art upon reading the detailed description of the preferred embodiments below. The drawings are only for the purpose of illustrating preferred embodiments and are not intended to limit the invention. Moreover, the same reference numerals are used throughout the drawings to refer to the same parts. In the drawings:

FIG. 1 is a schematic flowchart of a method for obtaining surface potential according to an embodiment of the present disclosure.

DETAILED DESCRIPTION OF THE INVENTION

Figure 2:
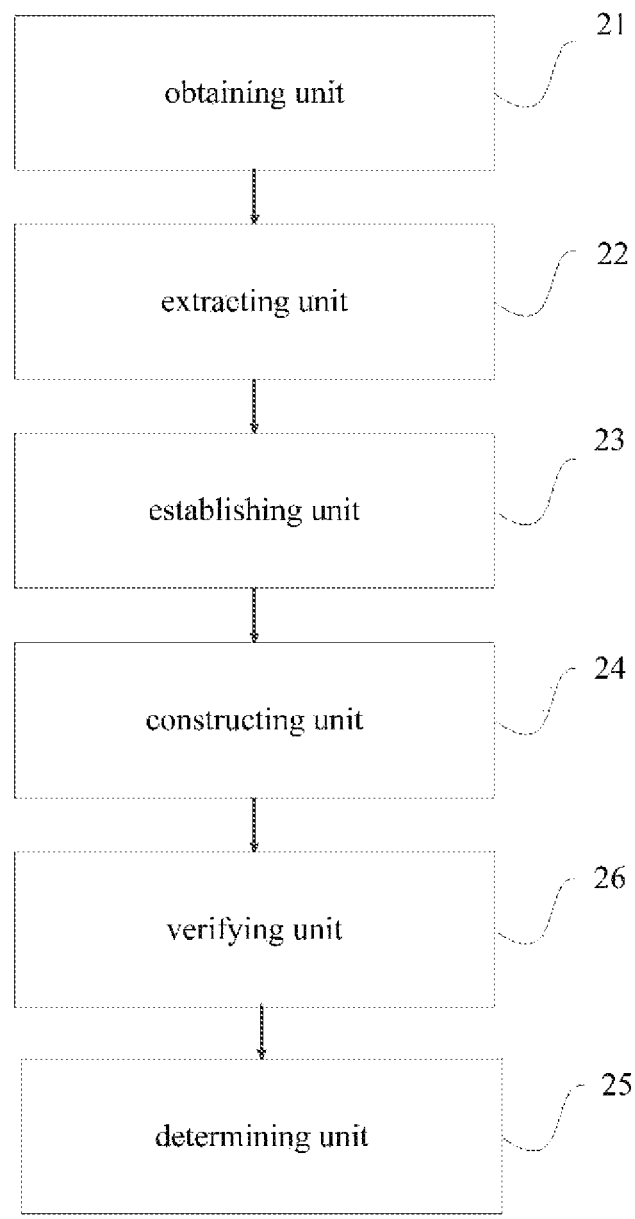
FIG. 2 is a schematic structural diagram of an apparatus for obtaining surface potential according to an embodiment of the present disclosure.

Hereinafter, exemplary embodiments of the present disclosure will be described in more detail with reference to the accompanying drawings. Although exemplary embodiments of the present disclosure are shown in the drawings, it should be understood that the present disclosure can be implemented in various forms and should not be limited by the embodiments set forth herein. On the contrary, these embodiments are provided to enable a thorough understanding of the present disclosure, and to fully convey the scope of the present disclosure to those skilled in the art.

The technical solution of the present disclosure will be further described in detail through the accompanying drawings and specific embodiments.

In one or more embodiments, a method for obtaining surface potential is provided. As shown in FIG. 1, the method may include step S110: obtaining parameter information of multiple target devices.

In order to establish a surface potential database, in this step, parameter information of multiple target devices needs to be obtained, and the parameter information includes: size, device structure, material parameter, and carrier mobility of each of the target devices at different temperatures. In some embodiments, the target devices may include devices fabricated by using conventional materials and devices fabricated by using some first new materials whose surface potentials have been measured and determined. Here, conventional materials are generally bulk materials, such as silicon, gallium nitride, etc.; and new materials include many types, generally being thin film materials, such as two-dimensional materials (graphene, single-layer molybdenum disulfide), nanotubes, etc. The surface potentials of some devices fabricated by using new materials have been measured and determined, then such new materials are called first new materials. Some new materials have never been used to fabricate a device, or a device has been fabricated but a surface potential of the device has never been measured, or the surface potential has been measured but never been determined, such new materials are called second new materials.

Here, the device structure generally includes: an annular gate structure, a vertical nano-gate structure, a single-layer or multi-layer thin-film structure, and so on. Material parameter includes: crystal structure, defect concentration, interface morphology, doping concentration, etc.

After obtaining the size, the device structure, and the material parameter of the multiple target devices, it is also necessary to obtain carrier mobility of each of the target devices at different temperatures, which can be obtained according to formula (1):

$$\mu(T) = \frac{qa}{k_B T} v_O \exp\left(-\frac{E_a}{k_B T}\right) \quad (1)$$

In formula (1), q represents elementary charge; a represents atomic separation; $k_B$ represents Boltzmann constant; T represents temperature; $v_O$ represents reciprocal of length of localized state; and $E_a$ represents activation energy of carrier transition.

The method may further comprise step S111: extracting surface potentials based on the size, the device structure, the material parameter, and the mobility of each of the target devices under corresponding operating conditions.

After obtaining the size, the device structure, the material parameter, and the carrier mobility of each of the multiple target devices, the surface potentials can be extracted under different operating conditions based on the size, the device structure, the material parameter, and carrier mobility of respective target devices. The operating conditions may include: operating current, operating voltage, and operating temperature, and so on.

For devices fabricated by using conventional materials, some software analytical models (such as Global TCAD or Mentor) can be used to extract surface potentials. Specifically, the software analytical models may receive the size, the device structure, the material parameter, the carrier mobility, and the operating conditions of each of the target devices, and then directly outputs corresponding surface potentials.

For devices fabricated by using some new materials, the surface potentials are existing data, which can be obtained directly.

The method may further comprise step S112: establishing a surface potential database based on the surface potentials and the parameter information.

After the surface potentials are obtained, a surface potential database can be established based on the surface potentials and the parameter information. The specific process is as follows:

establishing mapping tables between each of the surface potentials and the parameter information, specifically, establishing mapping tables between the surface potentials and the operating conditions, the sizes of the target devices, the device structures and the material parameters; storing the mapping tables into corresponding data blocks in a preset database to form the surface potential database.

For example, if a target device A has a surface potential B, a size C, with a device structure of annular gate structure, and a material parameter of defect concentration D, and the material is grapheme, then the above data can be stored in one table to form a mapping table. The surface potentials of other target devices can be handled in the same way, and finally multiple mapping tables can be obtained.

The method may further comprise step S113: constructing a surface potential analytical model according to neural network, based on the surface potential database.

After the surface potential database is established, a surface potential analytical model can be constructed according to neural network based on the surface potential database, and the specific process is as follows.

A surface potential training sample set may be determined based on the surface potential database. In some embodiments, various groups of data are extracted from the mapping tables of the surface potential database as training samples, and multiple groups of training samples form a training sample set. Then a hypothetical model provided by the neural network is used to learn the surface potential training sample set to obtain the learned data, and then data fitting on the learned data is performed to obtain a physical equation, and the physical equation is the surface potential analytical model. In some embodiments, the neural network may comprise an artificial neural network, a convolutional neural network, or a recurrent neural network.

In some embodiments, the neural network may include multiple layers, and each layer may include multiple neurons. If each training sample in the training sample set is used as an input value of the first layer of the neural network, then the output values of the first layer of the neural network are the input values of the second layer of neural network, and so on. The neural network will use the hypothetical model to calculate an output result according to the input of the last layer, and this output result will be the final physical equation.

In some embodiments, in the hypothetical model, weight values of respective parameters and intercept values of respective layers of the neural network are included. The parameters described herein are the device size, device structure, material parameter, etc. mentioned above.

The method may further comprise step S114: determining a surface potential of a device fabricated by using a second new material by using the surface potential analytical model.

After the surface potential analytical model is established, the surface potential analytical model needs to be verified to determine whether it meets a preset accuracy. The details are as follows.

A Schrödinger-Poisson equation is established based on one or more groups of data in the surface potential database. By utilizing the self-consistent solution, a first solution of the Schrödinger-Poisson equation can be obtained. Here, one or more groups of data are data in any mapping table or in multiple mapping tables. The establishment process and solving process of Schrödinger-Poisson equation are well-known in the art, and will not be described in detail here.

The same data are input into the surface potential analytical model to obtain a second solution of the surface potential analytical model, and a difference between the second solution and the first solution is obtained, and then the difference is used to verify the surface potential analytical model.

In some embodiments, using the difference to verify the surface potential analytical model may include: determining whether the difference is within a preset range. If it is, then it indicates that the accuracy of the surface potential analytical model can meet requirements. If it is not, it indicates that the accuracy of the surface potential analytical model cannot meet requirements. The preset range may be $10^{-9} \sim 10^{-7}$.

When the surface potential analytical model satisfies a preset accuracy, the surface potential analysis model can be used to determine the surface potential of a device fabricated by using a second new material.

In some embodiments, once the device structure, the size, the material parameter, etc. of the device fabricated by using the second new material are received and input into the surface potential analytical model, corresponding surface potential can be output.

Based on the same inventive concept, the present disclosure also provides an apparatus for obtaining the surface potential, as shown in the other embodiments.

In another embodiment, an apparatus for obtaining surface potential is provided. As shown in FIG. 2, the apparatus may include: an obtaining unit 21, an extracting unit 22, an establishing unit 23, a constructing unit 24, and a determining unit 25.

In order to establish a surface potential database, the obtaining unit 21 is configured to obtain parameter information of multiple target devices. The parameter information may include: size, device structure, material parameter, and carrier mobility of each of the target devices at different temperatures.

In some embodiments, the target devices may include devices fabricated by using conventional materials and devices fabricated by using first new materials whose surface potentials have been determined. Here, conventional materials are generally bulk materials, such as silicon, gallium nitride, etc., and the new materials include many types, generally being thin film materials, such as two-dimensional materials (graphene, single-layer molybdenum disulfide), nanotubes and so on. If a surface potential of a device fabricated by using a new material has been measured and determined, then this new material is called a first new material; and if a new material has never been used to fabricate a device, or a device has been fabricated but the surface potential thereof has never been measured, or the surface potential has been measured but has not been determined, such new material is called a second new material.

In some embodiments, the device structure may generally include: an annular gate structure, a vertical nano-gate structure, a single-layer or multi-layer thin-film structure, and so on. The material parameters may include: crystal structure, defect concentration, interface morphology, doping concentration, etc.

After the size, the device structure, and the material parameter of the multiple target devices are obtained, it is also necessary to obtain the carrier mobility of each of the target devices at different temperatures, which can be obtained according to formula (1):

$$\mu(T) = \frac{qa}{k_B T} v_O \exp\left(-\frac{E_a}{k_B T}\right) \quad (1)$$

In formula (1), q represents elementary charge, a represents atomic separation, $k_B$ represents Boltzmann constant, T represents temperature, $v_O$ represents reciprocal of length of localized state, and $E_a$ represents activation energy of carrier transition.

After the size, the device structure, the material parameter, and the carrier mobility of the multiple target devices are obtained, the extracting unit 22 is configured to extract the surface potentials based on the size, the device structure, the material parameter, and the carrier mobility of each of the multiple target devices under corresponding operating conditions. The operating conditions may include: operating current, operating voltage and operating temperature and the like.

For devices fabricated by using conventional materials, the extracting unit 22 may use some software analytical models (such as Global TCAD or Mentor) to extract the surface potentials. In some embodiments, the software analytical model may receive the size, the device structure, the material parameter and the carrier mobility as well as the operating conditions of each target device, and then directly outputs corresponding surface potentials.

For some devices fabricated by using new materials, the surface potentials are existing data, and the extracting unit 22 can directly obtain them.

After the surface potentials are obtained, the establishing unit 23 is configured to establish a surface potential database based on surface potentials and parameter information. The specific process is as follows.

The establishing unit 23 may be configured to establish mapping relationships between the surface potentials and parameter information. In some embodiments, the establishing unit 23 is configured to establish mapping tables between the surface potentials and the operating conditions, the sizes of the target devices, the device structures, and the material parameters. The mapping tables are stored in corresponding data blocks in a preset database to form the surface potential database.

For example, if a target device A has a surface potential B, a size C, a device structure of an annular gate structure, and a material parameter of defect concentration D, and the material is grapheme, then the above data can be stored in one table to form a mapping table. The surface potentials corresponding to other target devices can be handled in the same way, and finally multiple mapping tables can be obtained.

After the surface potential database is established, the constructing unit 24 is configured to construct a surface potential analytical model according to neural network based on the surface potential database. The specific process is as follows.

A surface potential training sample set is determined based on the surface potential database. In some embodiments, groups of data are extracted from the mapping tables of the surface potential database as training samples, and multiple groups of training samples can form a training sample set. Then a hypothetical model provided by the neural network is used to learn the surface potential training sample set to obtain the learned data, and then data fitting on the learned data is performed to obtain a physical equation, and the physical equation is the surface potential analytical model. In some embodiments, the neural network may comprise an artificial neural network, a convolutional neural network, or a recurrent neural network, and so on.

In some embodiments, the neural network may include multiple layers, and each layer may include multiple neurons. If each training sample in the training sample set is used as an input value of the first layer of the neural network, then the output values of the first layer of the neural network are the input values of the second layer of neural network, and so on. The neural network will use the hypothetical model to calculate an output result according to the input of the last layer, and this output result will be the final physical equation.

In some embodiments, in the hypothetical model, weight values of respective parameters and intercept values of respective layers of the neural network are included. The parameters described herein are the device size, device structure, material parameter, etc., mentioned above.

In some embodiments, in order to ensure the accuracy of the surface potential analytical model constructed, referring to FIG. 2, the apparatus may further comprise a verifying unit 26. After the surface potential analytical model is established, it is necessary to use the verifying unit 26 to verify the surface potential analytical model so as to check whether it meets a preset accuracy. The details are as follows.

A Schrödinger-Poisson equation is established based on one or more groups of data in the surface potential database, and by utilizing a self-consistent solution, a first solution of the Schrödinger-Poisson equation can be obtained. In some embodiments, one or more groups of data are data in any mapping table or in multiple mapping tables. The establishment process and solving process of Schrödinger-Poisson equation are well-known in the art, and will not be described here.

The same data are input into the surface potential analytical model to obtain a second solution of the surface potential analytical model, and a difference between the second solution and the first solution is obtained, and then the difference is used to verify the surface potential analytical model.

In some embodiments, using the difference to verify the surface potential analytical model may include: determining whether the difference is within a preset range. If it is, then it indicates that the accuracy of the surface potential analytical model can meet requirements. If it is not, it indicates that the accuracy of the surface potential analytical model cannot meet requirements. The preset range may be $10^{-9} \sim 10^{-7}$.

When it is determined that the surface potential analytical model satisfies a preset accuracy, the determining unit 25 can be configured to use the surface potential analytical model to determine the surface potential of a device fabricated by using a second new material.

In some embodiments, once the determining unit 25 receives the device structure, the size, the material parameter, etc., of the device fabricated by using the second new material as inputs into the surface potential analytical model, corresponding surface potential can be output.

The beneficial effects provided by the method and apparatus for obtaining surface potential according to the embodiments of the present disclosure may at least include the followings.

The disclosure provides a method and an apparatus for obtaining surface potential. The method may comprise: obtaining parameter information of multiple target devices, and wherein the parameter information may include: size, device structure, material parameter, and carrier mobility of each of the target devices at different temperatures, and the multiple target devices include: devices fabricated by using conventional materials and devices fabricated by using the first new materials whose surface potentials have been determined; extracting surface potentials based on the size, the device structure, the material parameter, and the mobility of each of the target devices under corresponding operating conditions; establishing a surface potential database based on the surface potential and the parameter information; constructing a surface potential analytical model according to neural network based on the surface potential database; determining the surface potential of a device fabricated by using a second new material by using the surface potential analytical model. Therefore, multiple target devices of different structures and different materials are used to obtain multiple surface potentials under different operating conditions; then a surface potential database is established based on these surface potentials, and a surface potential analytical model is constructed by using neural network, and a surface potential of a device fabricated by using a new material is determined by using the surface potential analytical model. Because the surface potential analytical model constructed is equivalent to an intelligent analytical model obtained by normalizing devices under various structures, various parameters, and various conditions, when a surface potential of a device fabricated by using a new material is determined by using the surface potential analytical model, a corresponding surface potential can be quickly determined according to some parameters of the device fabricated by using the new material, so that the surface potential can be obtained without complicated testing, improving the efficiency of obtaining surface potential, and also improving the efficiency of the overall research process when studying some characteristics of surface potential devices fabricated by using new materials with the surface potentials.

The above description relates only to the preferred embodiments of the present invention, and is not intended to limit the protection scope of the present invention. Any modification, equivalent substitution, and improvement made within the spirit and principle of the present invention shall be included within the scope of the present invention.

The invention claimed is:

1. A method for obtaining surface potential, comprising:
   obtaining parameter information of multiple target devices, wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined, and the conventional materials include bulk materials, and the first new materials include thin film materials;
   extracting surface potentials based on the size, the device structure, the material parameter and the mobility of each of the target devices under corresponding operating conditions;
   establishing a surface potential database based on the surface potentials and the parameter information;
   constructing a surface potential analytical model according to neural network based on the surface potential database; and
   determining the surface potential of a device fabricated by using a second new material by using the surface potential analytical model.

2. The method of claim 1, wherein obtaining carrier mobility of each of the target devices at different temperatures includes:
   obtaining the carrier mobility μ(T) according to a formula $$\mu(T) = \frac{qa}{k_B T} v_O \exp\left(-\frac{E_a}{k_B T}\right),$$

where q represents elementary charge, a represents atomic separation, $k_B$ represents Boltzmann constant, T represents temperature, $v_O$ represents reciprocal of length of localized state, and $E_a$ represents activation energy of carrier transition.

3. The method of claim 1, wherein the establishing a surface potential database based on the surface potentials and the parameter information includes:
 establishing mapping tables between the surface potentials and the parameter information; and
 respectively storing the mapping tables in corresponding data blocks in a preset database to form the surface potential database.

4. The method of claim 1, wherein constructing the surface potential analytical model according to neural network based on the surface potential database includes:
 determining a surface potential training sample set based on the surface potential database; and
 performing data fitting on the surface potential training sample set by using a hypothesis model provided by the neural network so as to obtain a physical equation, and the physical equation is the surface potential analytical model.

5. The method of claim 1, wherein after constructing the surface potential analytical model according to neural network based on the surface potential database, the method further comprises:
 establishing a Schrödinger-Poisson equation based on the surface potential database;
 obtaining a first solution of the Schrödinger-Poisson equation by using a self-consistent solution;
 obtaining a second solution of the surface potential analytical model;
 obtaining a difference between the second solution and the first solution; and
 verifying the surface potential analytical model by using the difference.

6. An apparatus for obtaining surface potential, comprising:
 an obtaining unit, configured for obtaining parameter information of multiple target devices, wherein the parameter information includes: size, device structure, material parameter, and carrier mobility of each of the target devices at different temperatures, and the multiple target devices include: devices fabricated by using conventional materials and devices fabricated by using first new materials whose surface potentials have been determined, and the conventional materials include bulk materials, and the first new materials include thin film materials;
 an extracting unit configured for extracting surface potentials based on the size, the device structure, the material parameter, and the mobility of each of the target devices under corresponding operating conditions;
 an establishing unit configured for establishing a surface potential database based on the surface potentials and the parameter information;
 a constructing unit configured for constructing a surface potential analytical model according to neural network based on the surface potential database; and
 a determining unit configured for determining the surface potential of a device fabricated by using a second new material by using the surface potential analytical model.

7. The apparatus of claim 6, wherein the second obtaining unit is specifically configured for:
 obtaining the carrier mobility µ(T) according to a formula $$\mu(T) = \frac{qa}{k_B T} v_0 \exp\left(-\frac{E_a}{k_B T}\right),$$

where q represents elementary charge, a represents atomic separation, $k_B$ represents Boltzmann constant, T represents temperature, $v_0$ represents reciprocal of length of localized state, and $E_a$ represents activation energy of carrier transition.

8. The apparatus of claim 6, wherein the establishing unit is specifically configured for:
 establishing mapping tables between the surface potentials and the parameter information; and
 respectively storing the mapping tables in corresponding data blocks in a preset database to form the surface potential database.

9. The apparatus of claim 6, wherein the constructing unit is specifically configured for:
 determining a surface potential training sample set based on the surface potential database; and
 performing data fitting on the surface potential training sample set by using a hypothesis model provided by the neural network so as to obtain a physical equation, and the physical equation is the surface potential analytical model.

10. The apparatus of claim 6, further comprising a verifying unit configured for:
 establishing a Schrödinger-Poisson equation based on the surface potential database;
 obtaining a first solution of the Schrödinger-Poisson equation by using a self-consistent solution;
 obtaining a second solution of the surface potential analytical model;
 obtaining a difference between the second solution and the first solution; and
 verifying the surface potential analytical model by using the difference.

* * * * *